United States Patent
Heckel (10) Patent No.: US 6,510,329 B2
(45) Date of Patent: Jan. 21, 2003

(54) DETECTION OF SENSOR OFF CONDITIONS IN A PULSE OXIMETER

(75) Inventor: Donald W. Heckel, Brighton, CO (US)

(73) Assignee: Datex-Ohmeda, Inc., Madison, WI (US)

(*) Notice: Subject to any disclaimer, the term of this patent is extended or adjusted under 35 U.S.C. 154(b) by 0 days.

(21) Appl. No.: 09/769,795

(22) Filed: Jan. 24, 2001

(65) Prior Publication Data

US 2002/0137995 A1 Sep. 26, 2002

(51) Int. Cl.[7] .................................. A61B 5/05
(52) U.S. Cl. ............................ 600/310; 128/920
(58) Field of Search .......................... 600/323, 310, 600/322, 336, 309, 328; 356/41, 40; 128/920

(56) References Cited

U.S. PATENT DOCUMENTS

| | | | | |
|---|---|---|---|---|
| 4,603,700 A | * | 8/1986 | Nichols et al. | 128/665 |
| 5,503,148 A | * | 4/1996 | Pologe et al. | 128/633 |
| 5,645,060 A | * | 7/1997 | Yorkey | 128/633 |
| 5,782,756 A | * | 7/1998 | Mannheimer | 600/322 |
| 6,035,223 A | * | 3/2000 | Baker, Jr. | 600/323 |

* cited by examiner

Primary Examiner—Willis R. Wolfe
Assistant Examiner—Mahmoud Gimie
(74) Attorney, Agent, or Firm—Marsh Fischmann & Breyfogle LLP (57) ABSTRACT

A system for detecting sensor off conditions in a pulse oximeter is disclosed. In one implementation, a detector off condition is identified based a volatility of a signal quality of a filtered detector signal. The detector signal is first filtered, for example, to reduce the effects of noise or to otherwise reduce or eliminate components extraneous to the signal of interest. The filtered signal is used to perform a volatility measurement. In this regard, a correlation coefficient may be computed relative to two channels of the filtered signal and a correlation coefficient may be monitored over a moving window to calculate variance values for the correlation coefficient. The resulting variance values may be used alone or in combination with other parameter values to identify a sensor off condition.

27 Claims, 6 Drawing Sheets

DATA POINT

DETECTION OF SENSOR OFF CONDITIONS IN A PULSE OXIMETER

FIELD OF THE INVENTION

The present invention relates in general to pulse oximetry and, in particular, to detecting and responding to unreliable signal conditions such as conditions associated with a sensor that is detached or misaligned or otherwise associated with a sensor that is not operating in a reliable measurement mode to measure a value related to oxygen saturation of arterial blood (collectively, "sensor off conditions").

BACKGROUND OF THE INVENTION

In the field of photoplethysmography, light signals corresponding with two or more different centered wavelengths may be employed to non-invasively determine various blood analyte values. By way of example, blood oxygen saturation ($SpO_2$) levels of a patient's arterial blood are monitored in pulse oximeters by measuring the absorption of oxyhemoglobin and reduced hemoglobin using red and infrared light signals. The measured absorption data allows for the calculation of the relative concentrations of reduced hemoglobin and oxyhemoglobin, and therefore $SPO_2$ levels, because reduced hemoglobin absorbs more light than oxyhemoglobin in the red band and oxyhemoglobin absorbs more light than reduced hemoglobin in the infrared band, and because the absorption relationship of the two analytes and the red and infrared bands is known.

To obtain absorption data, pulse oximeters include a probe that is releasably attached to a patient's appendage (e.g., finger, earlobe or the nasal septum). The probe directs red and infrared light signals to the appendage, or tissue-under-test. The light signals are provided by one or more sources which are typically disposed in the probe. A portion of the light signals is absorbed by the tissue-under-test and the intensity of the light transmitted through or reflected by the tissue-under-test (i.e., the modulated signal) is detected, usually by at least one detector that may also be located in the probe. The intensity of an output signal from the detector(s) is utilized to compute $SPO_2$ levels, most typically via a processor located in a patient monitor interconnected to the probe.

As noted above, the probe is releasably attached to the patient's appendage. In this regard, it is useful for the pulse oximeter to identify sensor off conditions such that the oximeter can provide an appropriate indication, e.g., by blanking or dashing the display and/or providing an alarm. Identifying such sensor off conditions is a particular concern in certain pulse oximetry environments. For example, certain disposable or single-use sensors are designed to wrap around a finger or other appendage of a patient and may be subject to sensor off conditions if not properly attached or otherwise due to patient movement. Similarly, pulse oximetry sensors used on pre-mature babies and other infants are difficult to keep properly attached/aligned because of limitations on attachment due to skin sensitivity concerns and also because of erratic movements of the infant. Even in other pulse oximetry environments, the sensor may become detached or misaligned.

The conventional approach to identifying such conditions is to analyze the signal output by the sensor. If the analyzed signal is determined to be inconsistent with an expected photoplethysmographic signal, a sensor off condition may be deemed to exist. However, such conditions are difficult to accurately identify for a number of reasons. First, the photoplethysmographic waveform or "pleth" is generally small in magnitude and can vary substantially from time to time and patient to patient. Accordingly, the pleth is difficult to characterize and is difficult to distinguish from various sources of noise. Moreover, if a detached sensor is swinging, vibrating or subject to other periodic motion, the resulting detector signal during a detector off condition may be modulated in a manner that mimics, to an extent, a pleth. Consequently, designers have devoted significant. effort to accurately detecting sensor off conditions.

In certain pulse oximetry products marketed by Datex-Ohmeda, a sensor off condition associated with a detached sensor has been detected based on the use of a correlation coefficient. Generally, a correlation coefficient is used in many fields to analyze how well two signals correlate to one another in terms of waveform and other signal characteristics. In the context of pulse oximetry, a correlation coefficient can be used to compare how well the signal from one channel (e.g., the red channel) compares to the signal from another other channel (e.g., the infrared channel). In the case of a pleth, a high level of correlation is anticipated. The noted Datex-Ohmeda products therefore monitor the correlation coefficient over time to obtain an indication of signal quality. If a low level of correlation is sustained over a time window a sensor off condition is deemed to exist. Specifically, if the mean of the correlation coefficient squared falls below a predetermined threshold continuously for a period of twelve seconds, a sensor off condition is detected.

SUMMARY OF THE INVENTION

The present invention relates to an improved system for detecting sensor off conditions. It has been observed that the signal quality of a pulse oximeter has a greater volatility during sensor off conditions than under conditions where a pleth is reliably measured. That is, sensor off conditions can be detected not only based on low levels of detected signal quality but, additionally or alternatively, based on changes in the level of detected signal quality. Indeed, it has been verified that. certain sensor off conditions can be more reliably identified using calculations involving signal quality volatility than using conventional techniques. The present invention thus allows for improved sensor off detection and response.

In accordance with one aspect of the present invention, a sensor off condition is detected based on a variance in detected signal quality. The associated method involves defining a measure of signal quality, monitoring the measure of signal quality over time, calculating a value related to variance of the signal quality measure, and identifying a sensor off condition based on the variance value. The measure of signal quality may be any suitable measure for quantifying the likelihood that a detected signal is a pleth. For example, the step of monitoring the signal quality may involve identifying two channels of the detector signal (e.g., red and infrared), determining a correlation coefficient based the signals of the two channels and monitoring the correlation coefficient with respect a moving window of a predetermined temporal length (e.g., several seconds).

Various mathematical models may be used to calculate a value related to variance or volatility of the signal quality measure. Such models may determine variance based on a comparison of pairs of data points, multiple data points or based on a mathematical/statistical analysis of all data within a selected window of data. For example, one such indication of variance is provided by computing a standard deviation of the signal quality over a time window. It will be appreciated that the time window for consideration of the variance value may be different than a time window for consideration of the signal quality measure. That is, the windows may be different in length and/or translated in time relative to one another. The calculated variance may be used alone or in combination with other parameters to identify a sensor off condition. For example, the sensor off condition may be based on comparing the variance value or a series of such values (or other values calculated therefrom) to a threshold.

In accordance with another aspect of the present invention, two different signal quality related values are used to identify a sensor off condition. As above, a measure of signal quality is defined and monitored. First and second values related to the signal quality measure are then calculated and used to identify a sensor off condition. In one implementation, the first value relates to a magnitude of the signal quality measure (e.g., an average of the measure over a time or data window) and the second value relates to a variance of the signal quality measure (e.g., a standard deviation of the measure over the same or a different time or data window). A ratio of the first and second values may be calculated and compared to a threshold or thresholds to identify a sensor off condition. Other system parameters may be considered in establishing or selecting a threshold level.

According to further aspect of the present invention, a detector off condition is identified based on a volatility of a signal quality of a filtered detector signal. The detector signal is first filtered, for example, to reduce the effects of noise or to otherwise reduce or eliminate components extraneous to the pleth of interest. For example, Blackman filter coefficients may be applied to a series of values of a channel signal data window to smooth out certain noise effects. The filtered signal is used to perform a volatility measurement. In this regard, a correlation coefficient may be computed relative to two channels of the filtered signal, and the correlation coefficient may be monitored over a moving window to calculate variance values for the correlation coefficient (e.g., standard deviation values). The resulting variance values may be used alone or in combination with other parameter values to identify a sensor off condition. It has been found that improved detection of sensor off conditions can be achieved by using such a variance value calculated based on a filtered signal.

BRIEF DESCRIPTION OF THE DRAWINGS

For a more complete understanding of the present invention and further advantages thereof, reference is now made to the following Detailed Description taken in conjunction with the drawings, in which.

DETAILED DESCRIPTION

In the following description, the invention is set forth in context of a system for detecting sensor off conditions in a pulse oximeter having at least a red and an infrared channel. Such channels may be separately provided at a processor, for example, via separate detectors and associated circuitry for each channel or via hardware filters interposed between a single sensor and the processor to separate the signals of the respective channels. Alternatively, a composite (multi-channel) signal may be received at a processor and then processed to obtain a digital signal (e.g., a series of values) corresponding to each channel. In addition, the invention is described below with respect to specific signal quality algorithms, signal quality variance algorithms and sensor off threshold calculations. Upon consideration of this disclosure, it will be appreciated that various aspects of the invention can be varied within the scope of the invention and have applicability beyond the sensor off applications described herein. Accordingly, the following description should be understood as setting forth exemplary implementations and applications of the invention and the invention is therefore is not limited to the specific description that follows.

Figure 1:
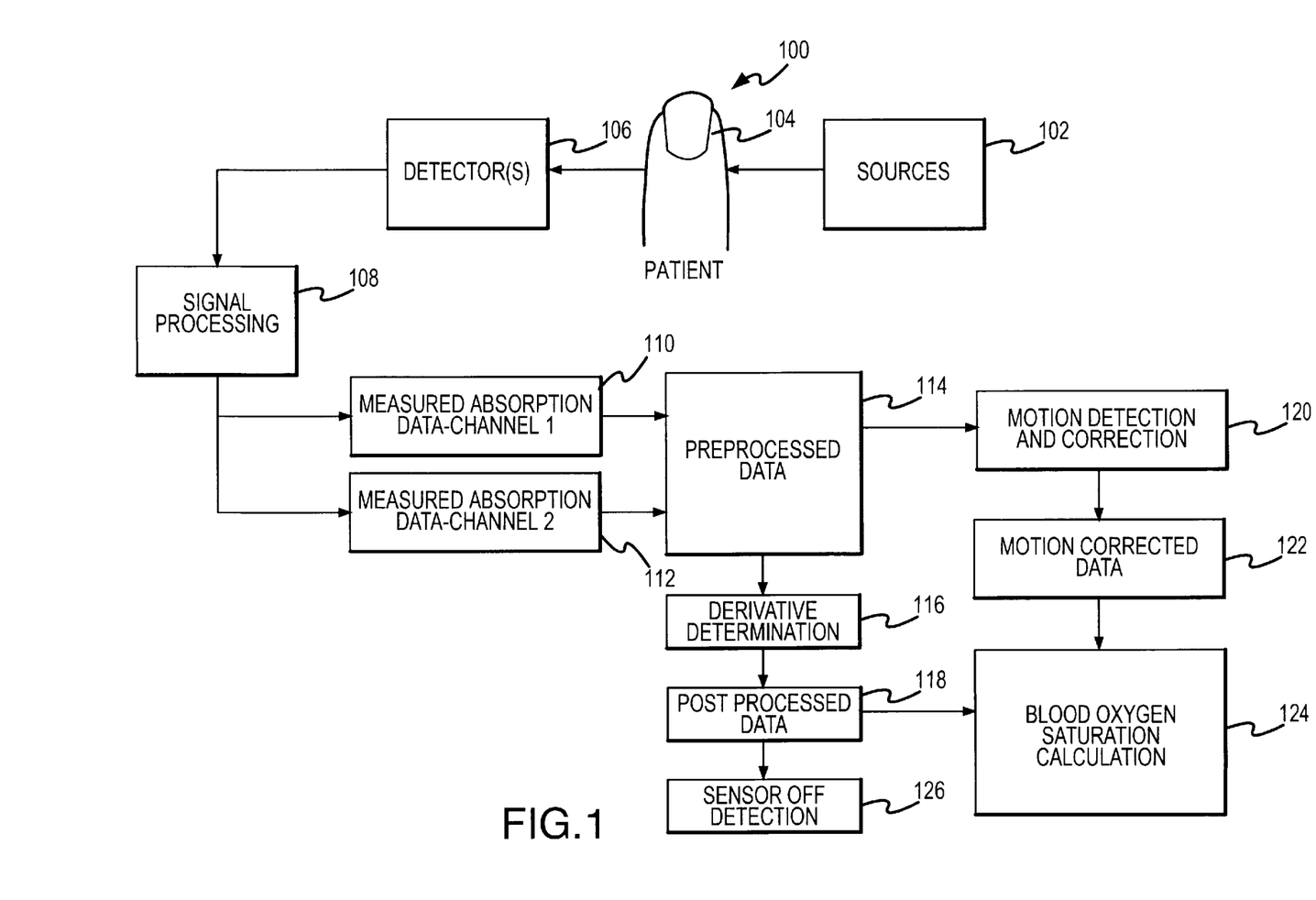
FIG. 1 is a schematic diagram of a pulse oximetry system in accordance with the present invention.

FIG. 1 illustrates a pulse oximetry system 100 in accordance with the present invention incorporating processing components 126 for detecting a sensor off conditions. As will be described in detail below, improved detector off condition detection is achieved by performing correlation coefficient and correlation coefficient variance calculations with respect to a filtered detector signal. In this regard, the following discussion includes a description of the pulse oximeter system, followed by a description of preferred filtering processes and concludes with a description of preferred sensor off detection systems.

Referring to FIG. 1, the illustrated pulse oximetery system 100 generally includes two or more light sources for transmitting light signals to an appendage of a patient. Light transmitted through or reflected from the patient's appendage is detected and blood oxygen saturation is determined based on absorption or attenuation of the signals. In the illustrated embodiment, the system 100 includes sources 102 which may be, for example, a red and an infrared transmitter. More than two sources operating at more than two wavelengths may be utilized, for example, for multi-component analysis. The signals from the sources 102 are transmitted to an appendage of the patient 104, in this case, a patient's finger and impinge on one or more detector(s) 106. The detector(s) 106 receive the optical signals and output an electrical detector signal representative of the received optical signals.

The detector signal is then processed by signal processing components 108. The signal processing components 108 may include various functional elements which may be embodied in hardware and/or software. For example, the signal processing components 108 may include an amplifier, an analog-to-digital converter, a de-multiplexer and other components for conditioning the signal. Such an amplifier may be utilized for various functions including converting the current signal from the detector into a voltage signal and filtering certain noise components. An analog-to-digital converter may be used to convert the received voltage signal into a series of digital values for processing by a digital processing unit. The de-multiplexer separates the detector signal into color channels e.g., red and infrared.

Accordingly, the signal processing components 108 in the illustrated embodiment provide two channels of measured absorption data 110 and 112. This data is stored in a preprocessed data buffer 114. The information stored in preprocessed data buffer 114 is used by a derivative determination module 116 to calculate derivatives as will be described in greater detail below. The resulting derivative values are stored in a postprocessed data buffer 118 and are used by components 126 for detecting sensor off conditions as described below.

The preprocessed data is also used by a motion detection correction module 120. Motion of the patient 104 may result in effective path length/attenuation changes of the transmitted signals that can result in errors in the blood oxygenation calculations if not addressed by the processing unit. In the illustrated embodiment, the motion detection and correction unit 120 accesses data from the preprocessed data buffer 114, and compensates for motion effects for improved accuracy. Data from each of the postprocessed data buffer 118 and the motion corrected data buffer 122 may be used by the blood oxygen saturation calculation module 124 to calculate a parameter related to blood oxygen saturation.

Figure 2:
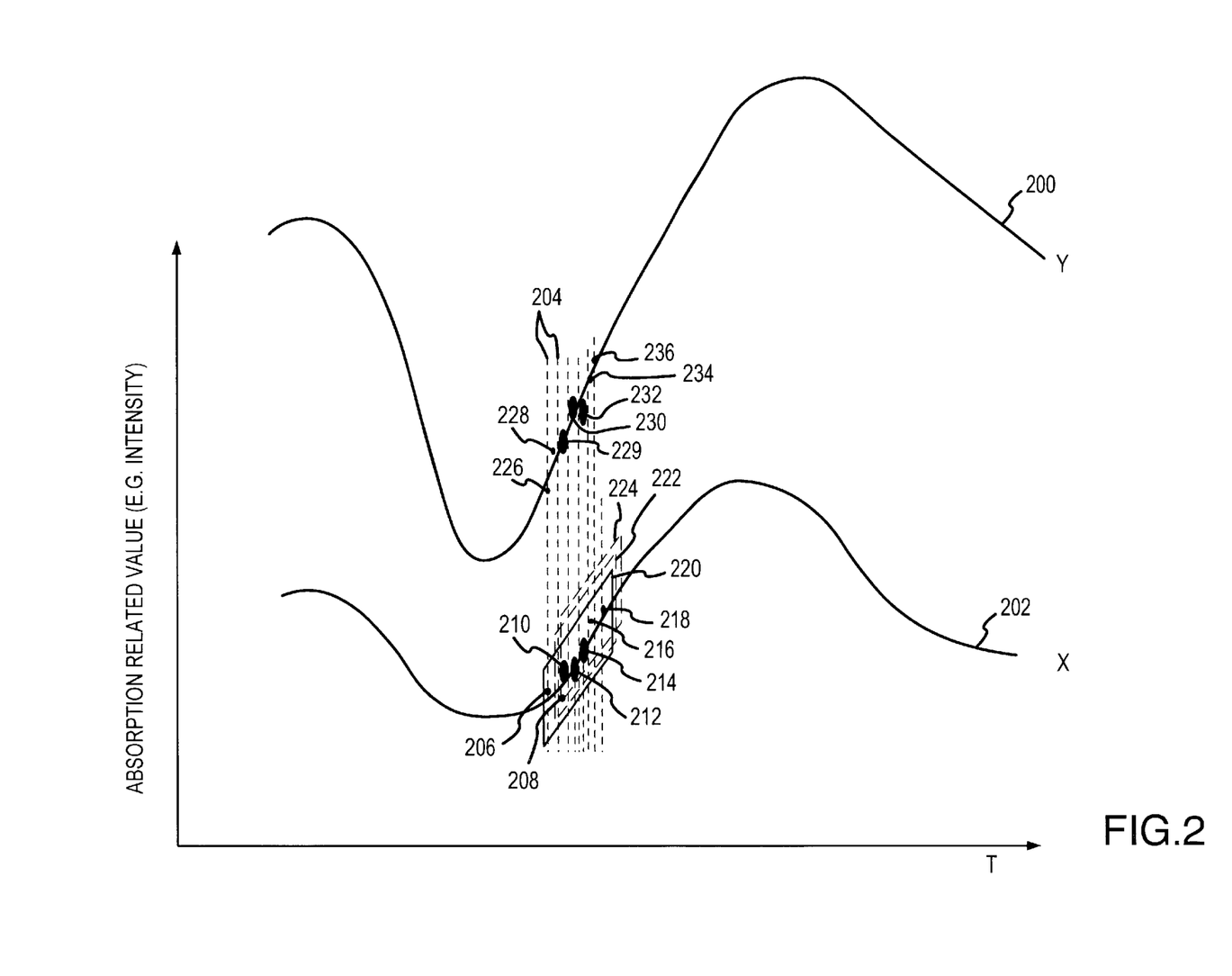
FIG. 2 is a graph illustrating a process for calculating differential values in accordance with the present invention.

FIG. 2 illustrates certain methodology for processing the measured absorption data. The measured absorption data generally includes a series of absorption related values (e.g. intensity) for a corresponding series of times for each of the two channels, in this case labeled channel X and channel Y. Blood oxygen saturation is proportional to the ratio of the normalized derivative of attenuation (NdAs) for the two channels. The NdAs can be calculated as discussed below. In FIG. 2, the signals 200 and 202 represent the pulsatile signal components of each of the channels. In reality, the measured absorption data for channel X includes a series of discrete absorption related values 206, 208, 210, 212, 214, 216 and 218 corresponding to particular times 204. Similarly, the measured absorption data for channel Y includes a discrete series of points 226, 228, 229, 230, 232, 234 and 236 associated with the same times 204.

In the illustrated implementation, NdAs for each of the channels are calculated using multiple data points. As shown, each of these data points is defined by a sample window 220, 222 and 224. Although the windows are only illustrated with respect to channel X, it will be appreciated that similar windows are employed to determine differential values for channel Y. In practice many data points may be included within each window. As will be understood upon consideration of the discussion below, samples across a given window are used to estimate a time derivative of attenuation or slope of the pulsatile signal for an instantaneous time interval corresponding to a center of the sampling window. This time derivative or slope is used in calculating an NdA. It will be appreciated that the window should therefore be small enough in relation to the expected pulsatile waveform so as to not unduly distort the calculated slope, but should be large enough to achieve the objective of reducing the impact of noise on the differential value calculation. In this regard, in a preferred implementation, a sampling rate of 30 samples per second is utilized and sampling window between about 0.1 to 0.5 seconds and, more preferably, between about 0.25 and 0.33 seconds is utilized. This corresponds to about 3 to 15 and, more preferably, about 7–10 samples per sampling window. For purposes of illustration, each of the illustrated windows 220, 222 and 224 are shown as including seven data points.

The data points within each window 220, 222 or 224 are used to establish a differential value nominally associated with the data sample about which the window is centered. Thus, the data points 206, 208, 210, 212, 214, 216 and 218 of window 220 are used to calculate a differential value such as an NdA for the center sample 212. As shown, a separate window is provided for each sample. Accordingly, even though multiple samples are utilized to calculate each differential value, a differential value is provided for each sample.

Various mathematical models can be used to calculate a differential value for a given sample based on the sample values within its window. In the illustrated implementation, the differential value is calculated based on a best-fit function analysis. Such a best-fit function analysis may involve, for example, a linear or non-linear regression analysis. A linear regression analysis allows for simplified processing and will be described in detail below.

In its simplest form, each of the samples within a window may be given equal weight in the linear regression analysis so as to determine the line which best fits all of the data points. The slope of this line thus provides a basic differential value for the center point of the window. However, certain processing advantages are achieved by converting this basic differential value into an NdA. This can be accomplished by calculating the NdA as the quotient of the slope of the best-fit line divided by an average of the DC components of the samples within the window, e.g., the sum of the DC components of samples 206, 208, 210, 212, 214, 216 and 218 divided by seven.

It has been found, however, that such an unweighted linear regression analysis not only smoothes out noise effects but can also smooth out abrupt signal changes corresponding to useful physiological information, for example, in the case of a patient with a rapid heart rate and therefore steep signal slopes. Accordingly, a preferred linear regression analysis involves weighting certain center points within the window more heavily than points closer to the window edges. This is illustrated graphically in FIG. 2 where the center samples 210, 212 and 214 are illustrated as being larger than the peripheral data points 206, 208, 216 and 218.

Figure 4:
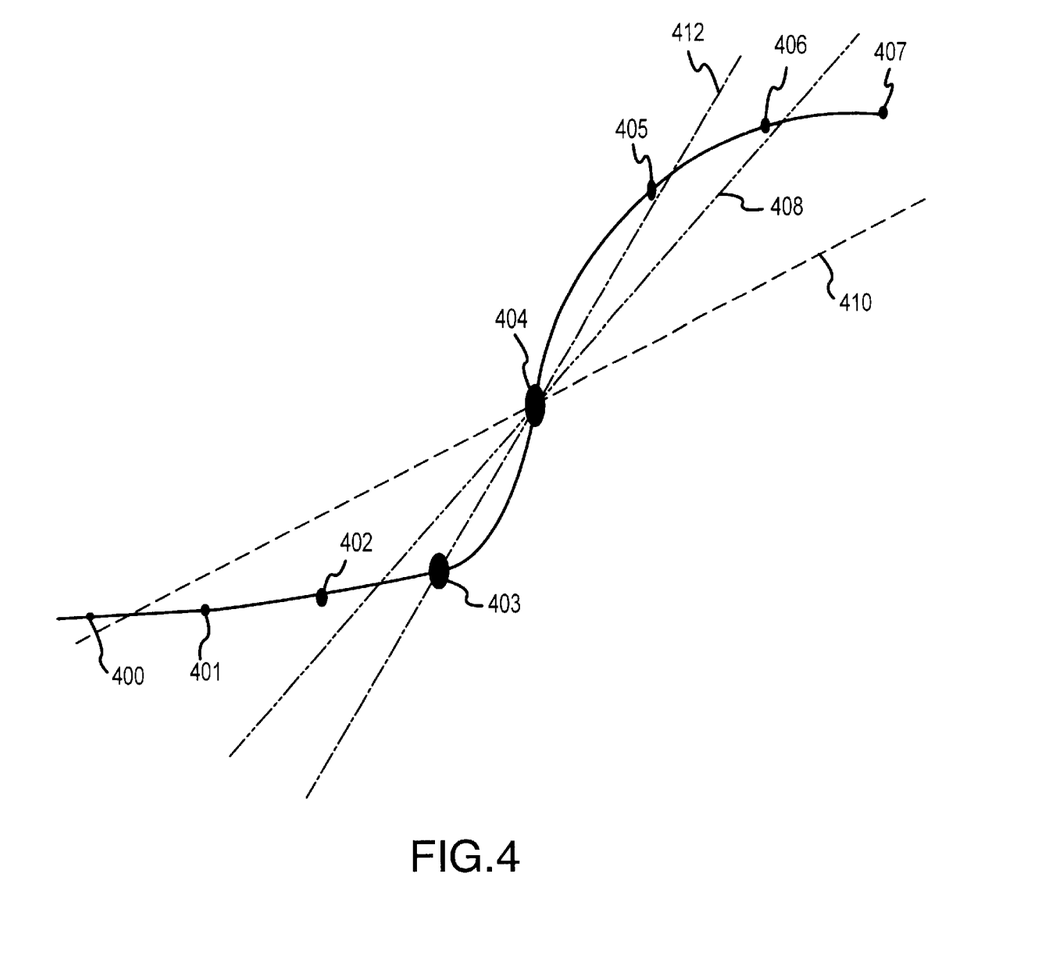
FIG. 4 is a graph illustrating the effect of weighting on the determined differential value in accordance with the present invention.

This effect is further illustrated in FIG. 4. Specifically, FIG. 4 shows a number of data points 400–407 of a given sampling window. Line 408 reflects the slope that would be calculated as the numerator of an NdA if only the two successive center data points 403 and 404 were used for the differential value calculation. Such a calculation is highly sensitive to noise. Best-fit line 410 illustrates the results of an unweighted linear regression analysis. Such an analysis typically derives the line 410 by a least square errors analysis wherein each data sample is given equal weight. That is, the linear regression algorithm attempts to minimize the value of the sum of the series of error terms for the data points 400–407 where each error term is the square of the deviation of the subject data point from the putative best-fit line. However, as noted above, such an unweighted window analysis is substantially affected by data points at the edges of the window, and may smooth out abrupt signal changes reflecting meaningful physiological data.

It has been found that improved results can be achieved by weighting the data points near the center of the window relative to those near the window edges 400, 407. It will be appreciated that the degree of weighting, e.g., the number of sample points weighted and the weighting factor applied to the weighted and/or "unweighted" sample points, can be selected so as to balance noise elimination against undesired smoothing. That is, the greater the weighting the more accurately the calculated differential values will track abrupt slope changes. However, greater weighting also reduces noise elimination. On the other hand, a lesser degree of weighting optimizes noise elimination but at the cost of allowing some degree of unwanted smoothing.

FIGS. 5a–5d show various models for weighting data points in the center of a sampling window relative to points at the window edges. The figures show such weighting graphically by plotting a weighting factor against point number, where points 1 and 8 represent the window edges and points 4 and 5 are at the center of the sampling window. The weighting factors can be applied as coefficients in the algorithm to determine the NdA. Specifically, an NdA can be calculated as a quotient where the numerator is the slope of a best-fit line drawn relative to the data points of a window and the denominator is an average value for the DC detector signal component.

As noted above, in an unweighted linear regression analysis, the best-fit line is defined by minimizing the sum of the error squared terms over a window. Weighting can be accomplished by applying a weighting coefficient to one or more (up to all) of the error squared terms used to define the best-fit line. By applying a larger weighting coefficient to the terms representing the middle of the window, any deviation between the putative best-fit line and these data points is amplified and thus factors heavily in the analysis. By contrast, deviations relating to points located nearer to the window edges are relatively diminished in the analysis. The weighting coefficients are also applied directly to the DC value for each data point in determining an average dc value for the denominator of the NdA.

As a result, as shown in FIG. 4, the slope of the line 408 determined by a weighted linear regression analysis may more closely match the slope of a line 412 drawn through the two center points 403 and 404, than would the slope of a line 410 determined using an unweighted linear regression analysis. Thus, the weighting achieves the desired effect of reducing the sensitivity to noise while not unduly smoothing out signal components corresponding to useful physiological information.

Figure 5A:
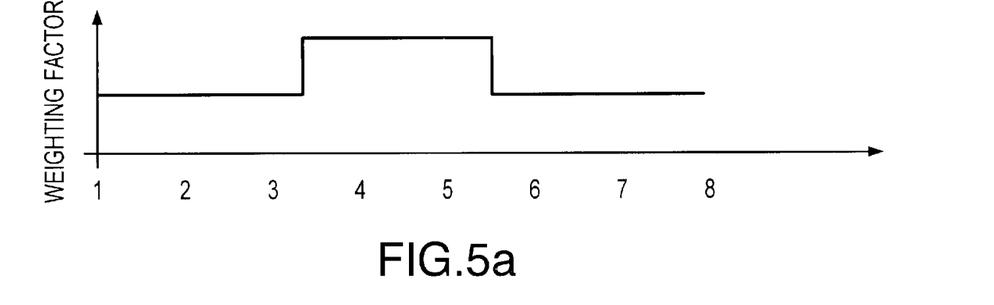
FIGS. 5a–5d illustrate various weighting models in accordance with the present invention.
Figure 5B:
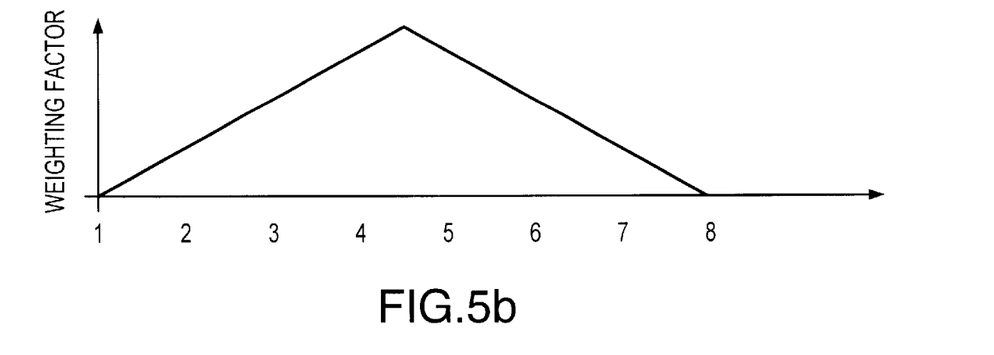
Figure 5C:
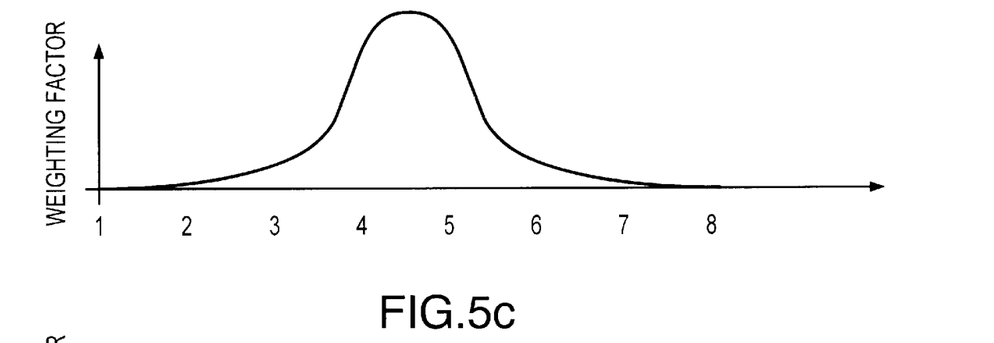
Figure 5D:
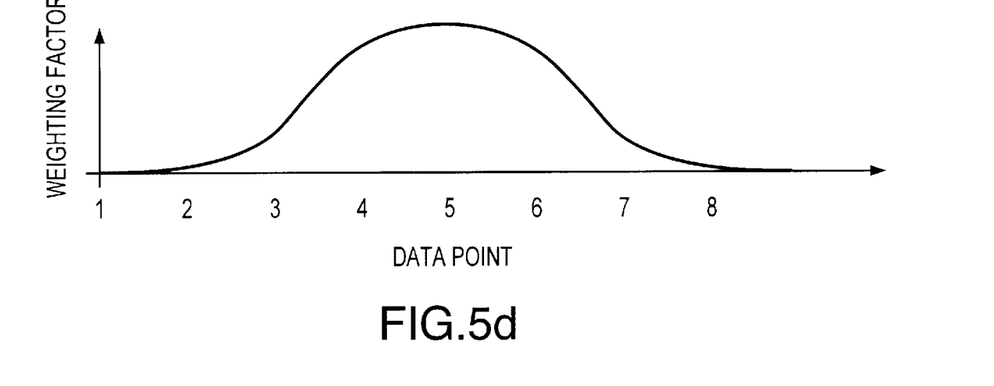

Referring to the weighting models of FIGS. 5a–5d, FIG. 5a illustrates a box window where points 1,2,3 and 6,7,8 are weighted by a first factor and the center points 4 and 5 are weighted by a second, greater factor. FIG. 5b illustrates a triangle window where points 1 and 8 are weighted by a factor of zero and, in between, the weighting factors increase, with the maximum weighting factor applied to the center points 4 and 5. FIG. 5c illustrates a Gaussian distribution of the weighting factor over the window, and 5d shows a sinusoidal of, more accurately, cosinusoidal distribution. It will be appreciated that many other weighting models are possible.

In a preferred implementation, the function of a low pass FIR filter window is utilized to achieve a weighting effect. Any low pass FIR filter window that does not apply negative weighting factors behaves well under the regression analysis. Examples are box, triangle, Gaussian, and Blackman filter windows, where the Blackman window has proved especially effective. Thus, although the functions of standard linear filters are used as weights, the resulting weighting algorithms are not linear. The weighting does not produce the same results as pre-filtering or post-filtering the window. The weighting produces the desired effect of producing a differential value of substantially full magnitude (little or no smoothing) while allowing a larger number of points in the regression analysis.

The following pseudo code implements a preferred NdA calculation.

```
Function [nda]=normdal (indata)
% [nda]=normda (indata)
winsz=9;
x=linspace (-winsz/2,winsz/2,winsz);
window=Blackman (winsz)';
window=window/sum (window); % nomalize
Sy=conv (indata,window);
Sx=0; % Sx=sum (x·window);
Sxx=sum (x·x·window);
Sxy=conv (indata,x·window);
Slope=Sxy/Sxx; % slope=(Sxy-Sx·Sy)·/(Sxx-Sx·Sx);
avr=Sy;
nda=slope ·/avr;
nda=nda (winsz:size(nda,2)-winsz);
``` wherein the terms "·" and "·/" represent vector multiplication and vector division, respectively.

By centering the window about "zero" time, the Sx term drops out. The SX^2 term, Sxx is a constant, as are the terms in the convolution with the vector x·window. The net result is code that has a few multiply/accumulates per window. As Sxx is a constant for both channels, the division by this term can be left out or done by multiplying by a 1/Sxx constant. Also, the average term (the average DC value used for normalization) is weighted by the same weighting by the regression terms in order to achieve the desired normalization effect.

Based on such processing, the NdAs for the red and infrared channels can be calculated on an ongoing basis during an analysis of a patient. As is well known, the blood oxygen saturation of the tissue-under-test is proportional to the ratio of the NdAs of the red and infrared channels. Accordingly, a blood oxygen saturation value, among other things, can be calculated based on the NdAs and displayed on a display of the pulse oximetry unit.

Figure 3:
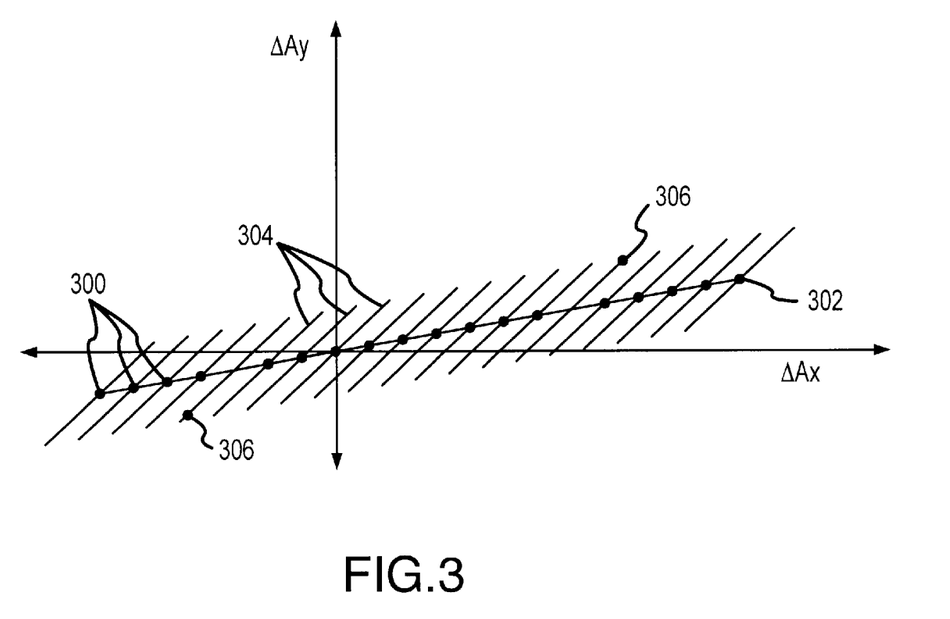
FIG. 3 is a graph illustrating a process for calculating an oxygen saturation value based on differential absorption ratios in accordance with the present invention.

FIG. 3 illustrates the process for calculating blood oxygen saturation based on the NdAs of the X and Y channels. In FIG. 3, the NdAs for the X and Y channels are designated by $\Delta A_x$ and $\Delta A_y$. Specifically, for each sample, the value of the NdA for the X channel is plotted against the value of the NdA for the Y channel to define a number of data points 300. The data points 300 define line 302. Mathematically, this line may be determined by using a best-fit function analysis such as a linear regression analysis on the data points 300. The slope of the line 302 is directly proportional to the blood oxygen saturation. It should be appreciated that the illustrated points are idealized in that they are precisely colinear. In reality, patient motion and other effects will typically cause the points 300 to be somewhat dispersed. In particular, motion will tend to cause an offset of the affected points 306 along a typically 45 degree offset line 304 as illustrated. This phenomenon can be utilized to identify motion affected data and to compensate for such effects. Thus, the blood oxygen saturation calculation involves determining derivative information as described above using pre-processed data. In the illustrated embodiment, motion affected data points 306 may be eliminated or de-weighted prior to performing the best-fit function analysis, e.g. linear regression analysis to determine the slope of the line 302.

As noted above, it is useful to identify sensor off conditions such that, for example, the display can be blanked and/or a visual, audio or other alarm can be triggered. This can be accomplished in accordance with the present invention by using the detector components 126 (FIG. 1) to perform a number of calculations related to a measure of signal quality. Specifically, it is expected that when a probe is properly attached and the source(s) and sensor(s) are properly aligned, and when the pulse oximeter is properly functioning to monitor tissue perfused with arterial blood, the red and infrared signals will generally have a high degree of correlation with respect to waveform and other signal characteristics. This is because the signals are affected by effective path length changes and other pulsatile attenuation factors that depend on common physiological influences. Moreover, it has been found that filtered signals defined for each channel also reflect a high degree of correlation under normal conditions, and may even reflect a higher degree of correlation due to the attenuation of uncorrelated noise from the raw signals.

In particular, improved results are obtained by calculating the variance values based on a digital signal that has been filtered to smooth out certain components of noise. As noted above, the NdAs can be calculated based on a moving window of channel signal values using filter coefficients that tend to weight values near the center of the window. Examples of filtering types that may be used include: Gaussian, box, triangle and Blackman filters, where Blackman filter coefficients have proved especially beneficial. In this manner, certain noise effects tend to be smoothed without undue smoothing out of signal components having physiological significance. The resulting digital signals, or series of NdA values for each channel, are used in the sensor off detection system 126 as described below. However, it will be appreciated that unfiltered signals or differently filtered signals may be employed.

The illustrated sensor off detection system 126 identifies a sensor off condition based on a correlation coefficient, a mean value of the correlation coefficient and a standard deviation of the correlation coefficient, all calculated based on moving windows of the NdA signal streams for the red and infrared channels. For N pairs of $(x_i, y_i)$, where $x_i$ is an NdA value of one channel for a given time and $y_i$ is an NdA value of the other channel for substantially the same time, a correlation coefficient may be computed by:

$$CC^2 = \frac{((N*\sum x_i y_i - \sum x_i y_i)*(N*\sum x_i y_i - \sum x_i y_i))}{(N*\sum x_i x_i - (\sum x_i * \sum x_i))*(N*\sum y_i y_i - (\sum y_i * \sum y_i))}$$

As discussed above, it has been found that the correlation coefficient is more volatile under a variety of sensor off conditions, e.g., when the probe has become detached. Accordingly, the sensor off detection system of the present invention utilizes a measure related to variance or volatility, for example, standard deviation. The standard deviation (Std) for an array of N values is given by:

$$\text{Std} = \sqrt{\frac{\sum (x_i - x_{mean})^2}{N-1}}$$

A preferred sensor off detection system according to the present invention utilizes both a value based on the correlation coefficient and a value based on variance. Once this quantity is defined, a threshold can be established theoretically or empirically to distinguish sensor off conditions from reliable signal conditions. It will be appreciated that various such quantities can be defined and the appropriate threshold range will vary accordingly. The sensor off detection system of the illustrated implementation utilizes the quantity, Q, defined as follows:

$$Q = \frac{\text{mean}(CC^2)}{\text{Std}(CC^2)}$$

Using this quantity, a threshold value or values can be defined to effectively identify sensor off conditions.

In some cases, this quantity Q, may be used in combination with other parameters in order to better identify sensor off conditions. Specifically, rather than performing a simple threshold comparison, a processor may look at both the quantity Q and a signal strength indicator as discussed below. It will be appreciated that different thresholds and different time windows for the sensor off detection analysis may be considered, for example, depending on the pulse oximetry system and the potential presence of any interfering effects.

Figure 6:
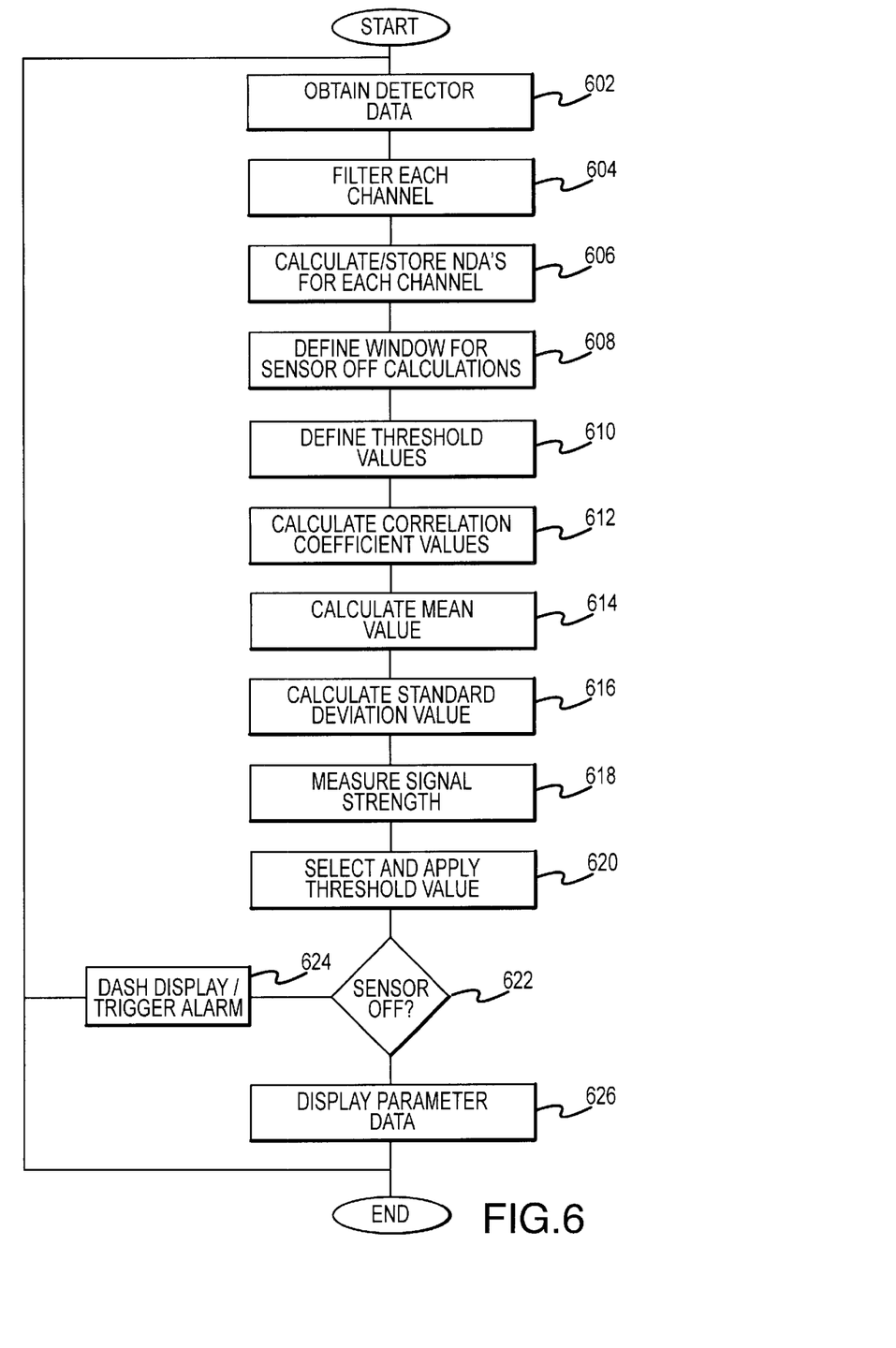
FIG. 6 is a flowchart illustrating a process for detecting sensor off conditions in accordance with the present invention.

The corresponding process for detecting and responding to sensor off conditions can be summarized by reference to the flowchart of FIG. 6. As shown, the process 600 is initiated by obtaining (602) detector data. Such detector data may be obtained at a processor in the form of a digital signal including components corresponding to each of the source channels. The received digital signal may be processed to obtain digital signals corresponding to each of the individual channels. In the illustrated process, each channel signal is filtered (604) such as by defining a window and applying filter coefficients, such as Blackman filter coefficients, to the series of values contained in the window. The NdAs for each channel can then be calculated (606) and stored for each channel as discussed above. The sensor off detection process can be performed using the NdA values obtained from the filtered detector signal.

The sensor off calculations are performed with respect to a moving predefined window of the NdA values. In the illustrated process, a window of, for example, 3 to 30 seconds may be selected. Good results have been obtained using a window of between about 7 and 10 seconds. Thus, the corresponding process involves defining (608) a time window for the sensor off calculations and defining (610) appropriate threshold values for identifying a sensor off condition. As noted above, different threshold values may be applied depending on, for example, the signal strength. In one implementation, if the computed signal strength is less than about $3/16^{th}$ of a maximum signal strength, then a signal quality of 5.0 is used to identify sensor off conditions. That is, a sensor off condition is detected if Q<5.0. Otherwise, a signal quality threshold of 2.5 is applied.

The values within the time window for each channel are then used to calculate (612) a correlation coefficient value for the data under analysis. Depending on the specific implementation, the correlation coefficient value may be the correlation coefficient itself or it may be the correlation coefficient squared or some other value derived or related to the correlation coefficient. From this correlation coefficient value, a mean of the correlation coefficient value for the window can be calculated (614). A standard deviation of the correlation coefficient value over the window can also be calculated (616). The signal strength is measured (618) in the illustrated implementation in order to select and apply (620) the appropriate threshold value. Based on this threshold analysis a sensor off condition can be identified (622). If a sensor off condition is detected, the parameter readings on the oximeter display can be dashed (624) and/or an alarm can be triggered. Otherwise, the parameter data is displayed (626) as normal. In either event, the process 600 can be repeated on a sample by sample basis or periodically throughout an oximetry procedure.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed:

1. A method for use in detecting and responding to a sensor off condition in a pulse oximetry system, said pulse oximetry system including a first source for providing a first channel signal associated with a first wavelength and a second source for providing a second channel signal associated with a second wavelength, said method comprising the steps of:

obtaining first and second detector signals associated with said first and second wavelengths, respectively;

monitoring said first and second detector signals over time period including a first time window and a second time window;

first determining a first correlation value relating to a first correlation between said first and second signals for said first time window;

second determining a second correlation value relating to a second correlation between said first and second signals for said second time window;

performing a comparison between said first and said second correlation values;

based on said comparison, determining a change value related to a change in said first correlation value relative to said second correlation value; and identifying a sensor off condition based on said change value.

2. The method of claim 1, wherein said monitoring step comprises monitoring said first and second signals over a time period of between about 3 seconds and 30 seconds.

3. The method of claim 1, wherein said monitoring step comprises monitoring said first and second signals over a time period of between about 7 seconds and 10 seconds.

4. The method of claim 1, wherein determining a plurality of correlation values comprises for each said correlation value correlating a plurality of individual data points from said first and second signals for a corresponding time window.

5. The method of claim 2, wherein calculating each said correlation value comprises correlating said data points from said corresponding time window wherein said corresponding time window is at least partially included within said monitored time period.

6. The method of claim 1, wherein said determining a value related to, change step comprises determining a mathematical deviation of at least one said correlation value from a normalized value associated with said plurality of correlation values.

7. The method of claim 6, wherein determining a mathematical deviation of said at least one correlation value comprises determining a standard deviation of said at least one correlation value from a mean correlation value associated with said plurality of correlation values.

8. The method of claim 1, wherein said identifying a sensor off condition comprises comparing at least one of said value related to change to and a normalized value associated with said plurality of correlation values to a predetermined threshold.

9. A method for use in detecting and responding to a sensor off conditions in a pulse oximetry system, said pulse oximetry system including a first source for providing a first channel signal associated with a first wavelength and a second source for providing a second channel signal associated with a second wavelength, comprising the steps of:

defining a measure of signal quality for a detected signal based on a comparative analysis of said first and second channel signals;

monitoring said measure of signal quality over a moving time window of a predetermined temporal length;

first calculating a reference value for said measure of signal quality for said moving time window;

second calculating a value related to variance of said measure of signal quality relative to said reference value; and identifying a sensor off condition based on said value related to variance.

10. The method of claim 9 wherein said step of defining a measure of signal quality comprises identifying at least one feature within a plethysrrographic signal.

11. The method of claim 10, wherein said step of monitoring said signal quality comprises identifying a correlation between said first and second channels within said plethysmographic signal.

12. The method of claim 11, wherein said step of monitoring comprises determining a plurality of correlation values between said channels for said moving time window.

13. The method of claim 12, wherein said step of first calculating comprises determining said reference value as a mean value for said correlation values for said moving time window.

14. The method of claim 13, wherein said step of second calculating a value related to variance comprises at least one of:

comparison of data points from at least one of said first and second channels with said reference value associated with said moving time window; and statistical comparison of at least one correlation value to said reference value associated with said moving time window.

15. A method for use in detecting and responding to a sensor off conditions in a pulse oximetry system, said pulse oximetry system including a detector for receiving light signals modulated by tissue of a patient, said method comprising the steps of:

obtaining first and second signals associated with first and second wavelengths of said light signals, respectively, from said detector;

filtering each said first and second signals to obtain a series of corresponding filtered values for each said wavelength, wherein filtering comprises performing a weighted average of at least a portion of each said signal over a moving time window associated with each said filtered value;

utilizing said corresponding filtered values for said first and second signals to determine a correlation value relating to a correlation between said first and second signals; and using said correlation value to identify a sensor off condition.

16. The method of claim 15, wherein said obtaining step comprises obtaining a plurality of data points for each said wavelength.

17. The method of claim 16, wherein for each said wavelength said step of filtering comprises performing a weighted average of said data points within said moving time window to determine said filtered values.

18. The method of claim 15, wherein said using step comprises using a first correlation values associated with a first moving time window and a second correlation value associated with a second time window to identify said sensor off condition.

19. The method of claim 18, wherein said step of identifying comprises comparing said first correlation value to said second correlation value.

20. The method of claim 19, wherein said step identifying comprises providing an sensor off indication when a change is said first correlation value relative to said second correlation value exceeds a predetermined threshold for a predetermined period.

21. A method for use in detecting and responding to a sensor off conditions in a pulse oximetry system, said method comprising the steps of:

defining a measure of correlation between first and second channels for a detected signal;

monitoring said measure of correlation between said first and second channels over a time window of a predetermined length;

determining a first value related to a magnitude of at least one of said first and second channels for said detected signal relative to said time window;

determining a second value related to a variance of said measure of correlation between said first and second channels relative to a normalized correlation value for said time window; and using said first value and said second value to identify a sensor off condition.

22. The method of claim 21, wherein said step of defining a measure of correlation comprises identifying at least one feature within a plethysmographic waveform for said first and second channels.

23. The method of claim 21, wherein said step of monitoring comprises determining a plurality of correlation values between said channels over said time window.

24. The method of claim 23, wherein said step of determining a second value related to variance further comprises determining a variance between at least a first correlation value and a reference value for said plurality of correlation values for said time window.

25. The method of claim 24, wherein said step of determining a second value comprises statistical comparison of said plurality of correlation values to a mean value of said plurality of correlation values for said time window.

26. The method of claim 21, wherein said step determining a first values comprises measuring an intensity of said detected signal.

27. The method of claim 21, wherein said first value is utilized to select a threshold for comparison with said second value.

* * * * *

UNITED STATES PATENT AND TRADEMARK OFFICE
CERTIFICATE OF CORRECTION

PATENT NO.    : 6,510,329 B2
DATED         : January 21, 2003
INVENTOR(S)   : Heckel It is certified that error appears in the above-identified patent and that said Letters Patent is hereby corrected as shown below:

<u>Column 2,</u>
Line 1, delete the word "photoplcthysmographic", and insert therefor
-- photoplethysmographic --;

<u>Column 11,</u>
Line 38, delete the word "signais", and insert therefor -- signals --;
Line 48, after the word "included", delete ".";
Line 51, after the word "to", delete " ,"; and <u>Column 12,</u>
Line 19, delete the word "plethysrrographic", and insert therefor
-- pleythysmographic --.

Signed and Sealed this

Third Day of February, 2004

JON W. DUDAS
*Acting Director of the United States Patent and Trademark Office*